United States Patent [19]

Nishihata et al.

[11] Patent Number: 4,555,404

[45] Date of Patent: Nov. 26, 1985

[54] SODIUM 7β-(2D-2-AMINO-2-CARBOXYETHYLTHI-OACETAMIDO)-7α-METHOXY-3-(1-METH-YL-1H-TETRAZOL-5-YL)THIOMETHYL-3-CEPHEM-4-CARBOXYLATE HEPTAHYDRATE AND PROCESS FOR ITS PREPARATION

[75] Inventors: Ken Nishihata; Katsuharu Iinuma; Hitoshi Yamada; Fumiya Hirano; Takashi Tsuruoka, all of Kanagawa, Japan

[73] Assignee: Meiji Seika Kaisha, Ltd., Tokyo, Japan

[21] Appl. No.: 495,236

[22] Filed: May 16, 1983

[30] Foreign Application Priority Data

May 14, 1982 [JP] Japan .................................. 57-80075

[51] Int. Cl.⁴ .................. C07D 501/36; A61K 31/545

[52] U.S. Cl. .................................... 514/201; 544/21; 544/26

[58] Field of Search ................... 424/246; 544/21, 25, 544/26, 27

[56] References Cited

U.S. PATENT DOCUMENTS 4,329,453  5/1982  Brodie et al. ......................... 544/25
4,357,331  11/1981  Iwamatsu et al. ..................... 544/21

*Primary Examiner*—Nicholas S. Rizzo
*Attorney, Agent, or Firm*—Sughrue, Mion, Zinn, Macpeak & Seas

[57] ABSTRACT

Sodium 7β-(2D-2-amino-2-carboxyethylthi-oacetamido)-7α-methoxy-3-(1-methyl-1H-tetrazol-5-yl)thiomethyl-3-cephem-4-carboxylate heptahydrate and a method of obtaining it from the corresponding carboxylate.

12 Claims, No Drawings

SODIUM 7β-(2D-2-AMINO-2-CARBOXYETHYLTHI-OACETAMIDO)-7α-METHOXY-3-(1-METHYL-1H-TETRAZOL-5-YL)THIOMETHYL-3-CEPHEM-4-CARBOXYLATE HEPTAHYDRATE AND PROCESS FOR ITS PREPARATION

FIELD OF THE INVENTION

This invention relates to sodium 7β-(2D-2-amino-2-carboxyethylthioacetamido)-7α-methoxy-3-(1-methyl-1H-tetrazol-5-yl)thiomethyl-3-cephem-4-carboxylate heptahydrate (hereinafter referred to merely as "heptahydrate") and a process for preparing it.

BACKGROUND OF THE INVENTION

The present inventors have formerly reported in Japanese Patent Application (OPI) No. 83791/80 (corresponding to U.S. Pat. No. 4,357,331) novel 7β-(2D-2-amino-2-carboxyethylthioacetamido)-7α-methoxy-3-(1-methyl-1H-tetrazol-5-yl)thiomethyl-3-cephem-4-carboxylic acid represented by the following formula (I):

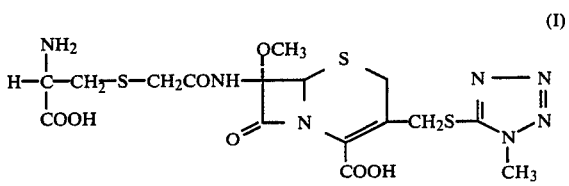

and its salt, such as the sodium salt of compound (I).

Compound (I) is prepared, for example, by the following reaction (A):

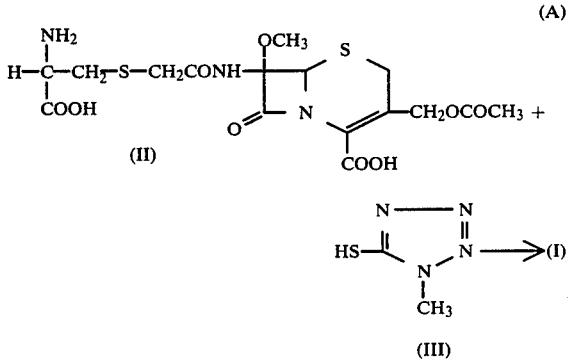

or by the following reaction (B):

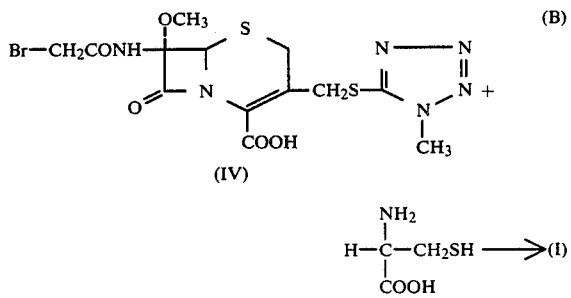

The compound (I) is effective against various bacteria such as gram-positive bacteria, gram-negative bacteria (except *Pseudomonas aeruginosa*), and anaerobic bacteria, thus having a wide antibacterial spectrum. Especially, it exhibits a strong antibacterial activity against gram-negative bacteria and, in comparison with other cephalosporins, it exhibits excellent antibacterial activity against *Bacteroides fragilis* and *Campylobacter jejuni*. In addition, it exhibits a strong bactericidal effect on *Escherichia coli*, *Klebsiella pneumoniae*, *Serratia marcescens*, etc. under short exposure. Further, it exhibits an antibacterial effect on bacteria in the stationary phase of growth.

The compound (I) possesses an excellent therapeutic effect on infectious diseases of mice induced by *Klebsiella pneumoniae*, *Proteus morganii*, *Escherichia coli*, *Serratia marcescens*, etc.

Acute toxicity testing of the compound (I) using mice revealed that $LD_{50}$ of the compound when intravenously administered to female mice is 5,200 mg/kg and that of the compound when intravenously administered to male mice is 6,100 mg/kg. In subacute toxicity testing and chronic toxicity testing using rats and dogs, the compound (I) was found show low toxidity. In a teratogenecity test and special toxicity tests, too, toxicity of the compound was found to be within an acceptable range.

Clinical studies revealed that blood level of the compound (I) after intravenous application reaches the highest level immediately after the injection and stands at an effective level for a long time, thus the compound showing good pharmacodynamic properties. Half-value period of the compound in blood is about 2.5 hours, and recovery from urine is 90 to 95%. These results suggest that the compound (I) will exhibit the same excellent antibacterial activity when administered to humans as it has exhibited in vitro and in laboratory animals.

However, while the compound (I) has the above-described excellent antibacterial activity, it is somewhat colored in appearance, darkening with passage of time, and also its potency is unstable at elevated temperatures, thus rendering compound (I) unsuitable as a practical medicine.

SUMMARY OF THE INVENTION

Objects of the present invention are to provide a compound having the same antibacterial activity as that of the compound (I) but having improved stability, thereby overcoming the above-described defects of compound (I), and a process for preparing such an improved compound.

A more specific object of the present invention is to provide a compound of excellent stability as to coloration and potency, while possessing the same antibacterial activity as that of compound (I).

Other objects of this invention will be apparent to the artisan from the Detailed Description of the Invention, hereinafter.

As a result of intensive investigations to attain the above-described objects, the present inventors have unexpectedly found that the sodium salt of the compound (I) crystallizes from its solution in water or from an aqueous organic solvent, to yield an extremely stable, crystalline heptahydrate. Various analyzing means have confirmed the heptahydrate structure. The "heptahydrate" does not possess the discoloration and potency loss problems of compound (I).

Therefore, a characteristic aspect of the present invention is novel sodium 7β-(2D-2-amino-2-carboxyethylthioacetamido)-7α-methoxy-3-(1-methyl-1H-tetrazol-5-yl)-thiomethyl-3-cephem-4-carboxylate heptahydrate and a process for precipitating crystals of the above-described heptahydrate by adjusting the pH of a solution of sodium 7β-(2D-2-amino-2-carboxyethylthioacetamido)-7α-methoxy-3-(1-methyl-1H-tetrazol-5-yl)thiomethyl-3-cephem-4-carboxylate in water or aqueous organic solvent to about 4.0 to 7.5.

DETAILED DESCRIPTION OF THE INVENTION

The heptahydrate of the present invention can be easily prepared directly from the reaction solution after completion of the reaction according to the foregoing reaction formula (A) or (B) or from its concentrate. In addition, it can be prepared, for example, by isolating the amorphous sodium salt of compound (I) which is obtained by the ordinary isolating methods such as column chromatography and subsequent freeze drying, dissolving the amorphous sodium salt in water or aqueous organic solvent, and crystallizing the heptahydrate from the resulting solution. In the present invention, the former preparation mode is preferable in view of the involved simplified preparation step.

The heptahydrate of the present invention is precipitated as crystals by adjusting pH of the solution of sodium salt of compound (I) in water or aqueous organic solvent to 4.0 to 7.5, preferably 6.2 to 6.8.

The above-described aqueous organic solvent is a mixture of water and a hydrophilic organic solvent (usually 60 volume % or less, depending upon the concentration of sodium salt of the compound (I)). The hydrophilic organic solvent includes, for example, alcohols such as ethanol, isopropanol, etc.; ethers such as tetrahydrofuran, dioxane, etc.; ketones such as acetone; amides such as N,N-dimethylformamide, N,N-dimethylacetamide, etc.; sulfoxides such as dimethylsulfoxide; and nitriles such as acetonitrile.

Adjustment of the pH is conducted by using an acid or a base. As the acid, there are illustrated, for example, inorganic acids such as hydrochloric acid, sulfuric acid, etc.; and organic acids such as acetic acid, oxalic acid, p-toluenesulfonic acid, etc. As the base, there are illustrated, for example, inorganic bases such as sodium hydroxide, sodium carbonate, sodium bicarbonate; etc.; and organic bases such as triethylamine, pyridine, benzylamine, etc.

In precipitating crystals of the heptahydrate from its solution, the concentration of sodium salt of the compount (I) is usually adjusted to 2 to 70 wt %, preferably 30 to 50 wt %, and the solution temperature preferably to 0° to 20° C., more preferably 0° to 5° C. Further, the temperature may be maintained, if necessary, at 0° to 5° C. for several hours to precipitate crystals.

The thus crystallized heptahydrate is collected in a conventional manner. For example, the end product is collected by filtration, washed, and dried. Drying of the crystals can be effected by air-drying or under reduced pressure, but is preferably effected in a stream of a sterilized inert gas (for example, sterilized nitrogen). However, long-time drying at an elevated temperature under reduced pressure is not suitable, because crystal water is partly removed.

Crystal structure of the heptahydrate of the present invention prepared by the above-described procedure was investigated on a four axes-type X-ray automatic diffractometer using CuKα to obtain the following data:

Molecular formula: $C_{16}H_{20}N_7O_7S_3Na \cdot 7H_2O$
Crystal system: triclinic
Space group: $P_1$
Lattice constant:
  a = 8.790 Å
  b = 10.992 Å
  c = 8.507 Å
  α = 104.9°
  β = 105.8°
  γ = 75.4°
Number of molecules in unit cell (Z): 1
Cell volume: 701.2 Å$^3$
Density: 1.58

The heptahydrate of the present invention possesses absolutely the same antibacterial activity as that of the compound (I). That is, it has a wide antibacterial spectrum, and shows particularly excellent antibacterial activity against gram-negative bacteria such as *Bacteroides fragilis* and *Campylobacter jejuni*. Various toxicity tests revealed that the heptahydrate shows the same toxicity as that of compound (I).

Furthermore, in comparison with the compound (I), the heptahydrate of the present invention does not become colored, showing excellent thermal stability. With respect to this point, Table 1 shows the results of tests on coloring properties and stability (potency survival ratio as compound (I)) of sodium salt (A) of compound (I) (amorphous) and the heptahydrate (B) of the present invention (crystalline), and Table 2 shows change with time in absorbance (indicating coloring properties) of A and B in aqueous solution (100 mg/ml) for a light of 440 nm in wavelength.

TABLE 1

|  | A | | B | |
|---|---|---|---|---|
|  | Potency Survival Ratio | Appearance | Potency Survival Ratio | Appearance |
| As the start | 100 | slightly yellowish white | 100 | white |
| After 2 months | | | | |
| 25° C. | 99 | slight yellow | 100 | no change |
| 40° C. | 95 | yellow | 100 | " |
| 50° C. | 91 | dark yellow | 98 | " |
| At the start | 100 | slight yellow | 100 | white |
| After 6 months | | | | |
| 13° C. | 100 | slight yellow | 100 | no change |
| 25° C. | 98 | yellow | 100 | " |
| 40° C. | 91 | dark yellow | 100 | almost no change |

TABLE 2

|  | At the Start | 1 min. | 3 min. | 5 min. | 10 min. | 30 min. | 60 min. | 120 min. |
|---|---|---|---|---|---|---|---|---|
| A | 0.066 | 0.123 | 0.174 | 0.204 | 0.235 | 0.258 | 0.264 | 0.259 |
| B | 0.002 | 0.001 | 0.001 | 0.001 | 0.001 | 0.003 | 0.011 | 0.017 |

As is clear from the above descriptions, the compound of the present invention shows an extremely excellent storage stability and undergoes less reduction in purity as compared to compound (I). Thus, the heptahydrate is useful as a medicine for treating bacteria-induced diseases. As to an administration manner for this purpose, the heptahydrate compound is administered parenterally by intravenous or intramuscular injection or in the form of suppository or orally in the form of tablets, powders, capsules or syrup, using conventional pharmaceutical carriers and excipients.

The present invention will now be illustrated in greater detail by way of the following examples of the present invention, which, however, are not to be construed as limiting the present invention in any way.

EXAMPLE 1

Two liters of a reaction solution containing 103 g (potency 99 g) of sodium 7β-(2D-2-amino-2-carboxyethylthioacetamido)-7α-methoxy-(1-methyl-1H-tetrazol-5-yl)-thiomethyl-3-cephem-4-carboxylate, obtained by the process described in Example 4 of Japanese Patent Application (OPI) No. 83791/80, was cooled to 0° to 5° C. 6N-HCl was added to this solution to adjust pH 3.0, and 1 liter of ethyl acetate was further added thereto. The resulting mixture was stirred for 15 minutes and, after allowing it to stand for 30 minutes, an aqueous layer was separated. 6N-NaOH was added to this aqueous layer to adjust pH 6.5. After concentration of this solution to a half volume, the pH was again adjusted to 6.5. Then the solution was concentrated to 440 ml, stirred at 0° to 5° C. for 2.5 hours, and stored at 5° C. overnight. The crystals thus formed were collected by filtration, and washed with 110 ml each of a cold (0° to 5° C.) 50% aqueous isopropyl alcohol two times, followed by removing the remaining solvent to obtain 130 g of crude primary crystals.

The thus obtained crude crystals were dissolved to warm (45° to 50° C.) 140 ml of pyrogen free water (hereinafter abbreviated as PFW). The resulting solution was filtered, and the filtrate was stirred at 0° to 5° C. for 3 hours, then stored at 5° C. overnight. Crystals thus formed were collected by filtration, washed with 150 ml of a cold (0° to 5° C.) 50% aqueous isopropyl alcohol, freed of the solvent, and air-dried for 5 to 6 hours to give 103 g of white crystals as heptahydrate. Potency: 79 g. Yield: 80%.

$\lambda_{max}{}^{H_2O}=273$ nm ($E_{1\ cm}{}^{1\%}=166$)
$[\alpha]_D{}^{25}=+67.2°$ (c=0.5, water)
$H_2O$ content calculated for $C_{16}H_{20}N_7O_7S_3Na \cdot 7H_2O$: 18.9%
$H_2O$ content found: 19.6% (Karl Fischer's method)
pH: 5.3 (10% w/v)

EXAMPLE 2 pH of a reaction solution obtained in the same manner as in Example 1 was adjusted to 4.0 with 6N-NaOH at 0° to 5° C. This solution was concentrated to 440 ml, stirred at 0° to 5° C. for 2.5 hours, and stored at 5° C. overnight. Crystals thus formed were collected by filtration, and washed in the same manner as in Example 1 to obtain 100 g of crude primary crystals.

Then, the thus obtained crude crystals were dissolved in 110 ml of PFW under heating to 45° to 50° C., and filtered. The filtrate was stirred at 0° to 0° C. for 3 hours, and stored at 5° C. overnight. Crystals thus formed were collected by filtration, washed with 120 ml of a cold (0° to 5° C.) 50% aqueous isopropyl alcohol and dried to obtain 78 g of white crystals as heptahydrate.

$\lambda_{max}{}^{H_2O}=273$ nm ($E_{1\ cm}{}^{1\%}=159$), water corrected value 196
$[\alpha]_D{}^{25}=+66.8°$ (c=0.5, water), water-corrected value +82.4°
$H_2O$ content found: 18.9% (Karl Fischer's method)
pH: 5.1 (10% w/v)

EXAMPLE 3 pH of a reaction solution obtained in the same manner as in Example 1 was adjusted to 7.5 with 6N-NaOH at 0° to 5° C. This solution was concentrated to 440 ml, stirred at 0° to 5° C. for 2.5 hours, and stored at 5° C. overnight. Crystals thus formed were collected by filtration and washed in the same manner as in Example 1 to obtain 109 g of crude primary crystals.

Then, the thus obtained crude crystals were dissolved in 120 ml of PFW under heating, and filtered. The filtrate was treated in the same manner as in Example 1, washed with 130 ml of a cold (0° to 5° C.) 50% aqueous isopropyl alcohol and dried to obtain 88 g of white crystals as heptahydrate.

$\lambda_{max}{}^{H_2O}=273$ nm ($E_{1\ cm}{}^{1\%}=160$), water-corrected value 196
$[\alpha]_D{}^{25}=+65.6°$ (c=0.5, water), water-corrected value +80.7°
Water content found: 18.7% (Karl Fischer's method)
pH: 5.4 (10% w/v)

EXAMPLE 4 pH of 500 ml of a reaction solution obtained in the same manner as in Example 1 was adjusted to 6.5 with 6N-HCl. This solution was concentrated to 125 ml, and 250 of a cold (0° to 5° C.) 50% aqueous isopropyl alcohol was dropwise added thereto under stirring, then stirred at 0° to 5° C. for 1 hour. Crystals thus formed were collected by filtration, washed once with 125 ml of a cold 50% aqueous isopropyl alcohol, then twice with 125 ml each of a cold 50% aqueous ethyl alcohol, and dried to obtain 24.5 g of white crystals as heptahydrate.

$\lambda_{max}{}^{H_2O}=273$ nm ($E_{1\ cm}{}^{1\%}=163$), water correction value 201
$[\alpha]_D{}^{25}=+67.2°$ (c=0.5, water), water correction value +83.0°
Water content found: 19.0% (Karl Fischer's method)
ph: 5.2 (10% w/v)

EXAMPLE 5

By treating in the same manner as in Example 4 except for using a 50% aqueous ethyl alcohol in place of a 50% aqueous isopropyl alcohol for precipitating crystals, 25.4 g of white crystals were obtained. Potency: 18.6 g.

$\lambda_{max}{}^{H_2O}=273$ nm ($E_{1\ cm}{}^{1\%}=162$), water correction value 200
$[\alpha]_D{}^{25}=+66.6°$ (c=0.5, water), water correction value +82.0°
$H_2O$ content found: 18.8% (Karl Fischer's method)
pH: 5.3 (10% w/v)

EXAMPLE 6

One liter of a reaction solution obtained in the same manner as in Example 1 was concentrated to about 500 ml. pH of this concentrate was adjusted to 6.8. Then, the concentrate was passed through 5 liters of a DIAION HP-20 column to adsorb the compound thereon, followed by developing with water to collect 500 ml portions or fractions. Fractions containing the reaction product were collected (12.5 liters), and concentrated to 100 ml. This concentrate was stirred at 0° to 5° C. for 4 hours, then stored at 0° to 5° C. overnight. Crystals thus formed were collected by filtration, washed with 120 ml of a cold (0° to 5° C.) 50% aqueous isopropyl alcohol, and dried to obtain 43 g of white crystals as heptahydrate.

$\lambda_{max}^{H2O} = 273$ nm ($E_1{}_{cm}{}^{1\%} = 157$), water correction value 194

$[\alpha]_D^{25} = +67°$ (c=0.5, water), water correction value +82.6°

H$_2$O content found: 18.9% (Karl Fischer's method)

pH: 5.4 (10% w/v)

EXAMPLE 7

350 g of freeze-dried powder of the sodium salt of the compound (I) (water content: 4%; potency: 322 g) was dissolved in 700 ml of water. 1400 ml of a cold (0° to 5° C.) 50% aqueous isopropyl alcohol was added thereto, and the resulting solution was stirred at 0° to 5° C. for one hour. Crystals thus formed were collected by filtration, washed once with 700 ml of a cold 50% aqueous isopropyl alcohol, then twice with 700 ml each of a cold 50% aqueous ethyl alcohol, and dried to obtain 334 g of white crystals as heptalydrate. Potency: 250 g.

$\lambda_{max}^{H2O} = 273$ nm ($E_1{}_{cm}{}^{1\%} = 163$), water correction value 202

$[\alpha]_D^{25} = +65.4°$ (c=0.5, water), water correction value +81°

H$_2$O content found: 19.3% (Karl Fischer's method)

pH: 5.3 (10% w/v)

EXAMPLE 8

1 kg of freeze-dried powder of the sodium salt of the compound (I) (water content: 4%; potency: 920 g) was dissolved in 1.2 liters of water at 45° to 50° C., and 25 g of active carbon was added thereto. After stirring for 15 minutes, the mixture was filtered. The filtrate was further stirred at 0° to 5° C. for 2.5 hours, and stored at 5° C. overnight. Crystals thus formed were collected by filtration, washed with a cold 50% aqueous isopropyl alcohol, and dried to obtain 962 g of white crystals as heptahydrate. Potency: 736 g.

$\lambda_{max}^{H2O} = 273$ nm ($E_1{}_{cm}{}^{1\%} = 160$), water correction value 198

$[\alpha]_D^{25} = +65.8°$ (c=0.5, water), water correction value +81.3°

H$_2$O content found: 19.1% (Karl Fischer's method)

pH: 5.4 (10% w/v)

Variations of the invention will be apparent to the skilled artisan.

What is claimed is:

1. Sodium 7$\beta$-(2D-2-amino-2-carboxyethylthioacetamido)-7$\alpha$-methoxy-3-(1-methyl-1H-tetrazol-5-yl)thiomethyl-3-cephem-4-carboxylate heptahydrate.

2. A process for preparing sodium 7$\beta$-(2D-2-amino-2-carboxyethylthioacetamido)-7$\alpha$-methoxy-3-(1-methyl-1H-tetrazol-5-yl)thiomethyl-3-cephem-4-carboxylate heptahydrate, which comprises forming a solution of sodium 7$\beta$-(2D-2-amino-2-carboxyethylthioacetamido)-7$\alpha$-methoxy-3-(1-methyl-1H-tetrazol-5-yl)thiomethyl-3-cephem-4-carboxylate in water or aqueous organic solvent; adjusting the pH of the solution to about 4.0 to 7.5 and then precipitating said heptahydrate as crystals.

3. The process of claim 2 wherein the pH of the solution is adjusted to be within about 6.2 to 6.8.

4. The process of claim 2 wherein the temperature of the pH-adjusted solution is maintained at about 0° to 20° C. to cause precipitation of the heptahydrate crystals.

5. The process of claim 3 wherein the temperature of the pH-adjusted solution is maintained at about 0° to 20° C. to cause precipitation of the heptahydrate crystals.

6. The process of claim 4 wherein the temperature of the pH-adjusted solution is maintained at about 0° to 5° C.

7. The process of claim 5 wherein the temperature of the pH-adjusted solution is maintained at about 0° to 5° C.

8. The process of claim 2 wherein the concentration of sodium 7$\beta$-(2D-2-amino-2-carboxyethylthioacetamido)-7$\alpha$-methoxy-3-(1-methyl-1H-tetrazol-5-yl)thiomethyl-3-cephem-4-carboxyate in the solution is 2 to 70 wt %.

9. The process of claim 8 wherein the concentration is 30 to 50 wt %.

10. The process of claim 2 wherein the precipitated crystals are collected by filtration, washed and dried.

11. The compound of claim 1 in crystalline form.

12. A pharmaceutical preparation comprising an antibacterially-effective amount of the compound of claim 1 and a pharmaceutically acceptable carrier.

* * * * *